United States Patent [19]
Boutet et al.

[11] Patent Number: 5,105,079
[45] Date of Patent: Apr. 14, 1992

[54] SPLIT V-ROOF MIRROR COLLECTOR HAVING IMPROVED COLLECTION EFFICIENCY

[75] Inventors: John C. Boutet, Rochester; Michael B. Brandt, Walworth, both of N.Y.

[73] Assignee: Eastman Kodak Company, Rochester, N.Y.

[21] Appl. No.: 631,619

[22] Filed: Dec. 21, 1990

[51] Int. Cl.[5] ............................................. G01J 1/00
[52] U.S. Cl. .............................. 250/228; 250/227.31; 250/327.2
[58] Field of Search ............... 250/227.31, 228, 327.2, 250/337, 348; 350/96.28

[56] References Cited

U.S. PATENT DOCUMENTS

| | | | |
|---|---|---|---|
| Re. 31,847 | 3/1985 | Luckey | 250/327.2 |
| 4,346,295 | 8/1982 | Tanaka et al. | 250/327.2 |
| 4,629,890 | 12/1986 | Goto et al. | 250/327.2 F |
| 4,742,225 | 5/1988 | Chan | 250/327.2 F |
| 4,743,758 | 5/1988 | Chan et al. | 250/327.2 D |
| 4,743,759 | 5/1988 | Boutet | 250/327.2 |
| 4,833,325 | 5/1989 | Torii et al. | 250/327.2 D |
| 4,867,530 | 9/1989 | Sedlmayr | 350/96.28 |

Primary Examiner—David C. Nelms
Assistant Examiner—S. Allen
Attorney, Agent, or Firm—William F. Noval

[57] ABSTRACT

A light collector collects and detects light emitted from a photostimulable phosphor medium such as a phosphor sheet in a photostimulable phosphor imaging system. The collector includes a vertical mirror extending the width of the phosphor sheet; and a V-roof mirror having upper and lower mirrors forming an apex facing the vertical mirror. The vertical mirror and V-roof mirror form slots for passing a scanning beam of stimulating radiation through the collector to the surface of the photostimulable phosphor sheet and for admitting emitted light from the phosphor sheet into the collector. The vertical mirror and V-roof mirror form a substantially triangular cross-section which diminishes in size from one edge of the phosphor sheet to the other edge thereof. A photodetector is positioned at the large end of the triangular collector for receiving light emitted from the photostimulable phosphor sheet and for generating an electrical signal in response thereto. A vertical mirror is located below the photodetector to increase collection efficiency. Alternatively, the photodetector is located at an aperture in the vertical mirror and an exit deflector mirror closes off the large end of the V-roof mirror. The photodetector may also be positioned at angles other than 90° to the vertical mirror.

6 Claims, 7 Drawing Sheets

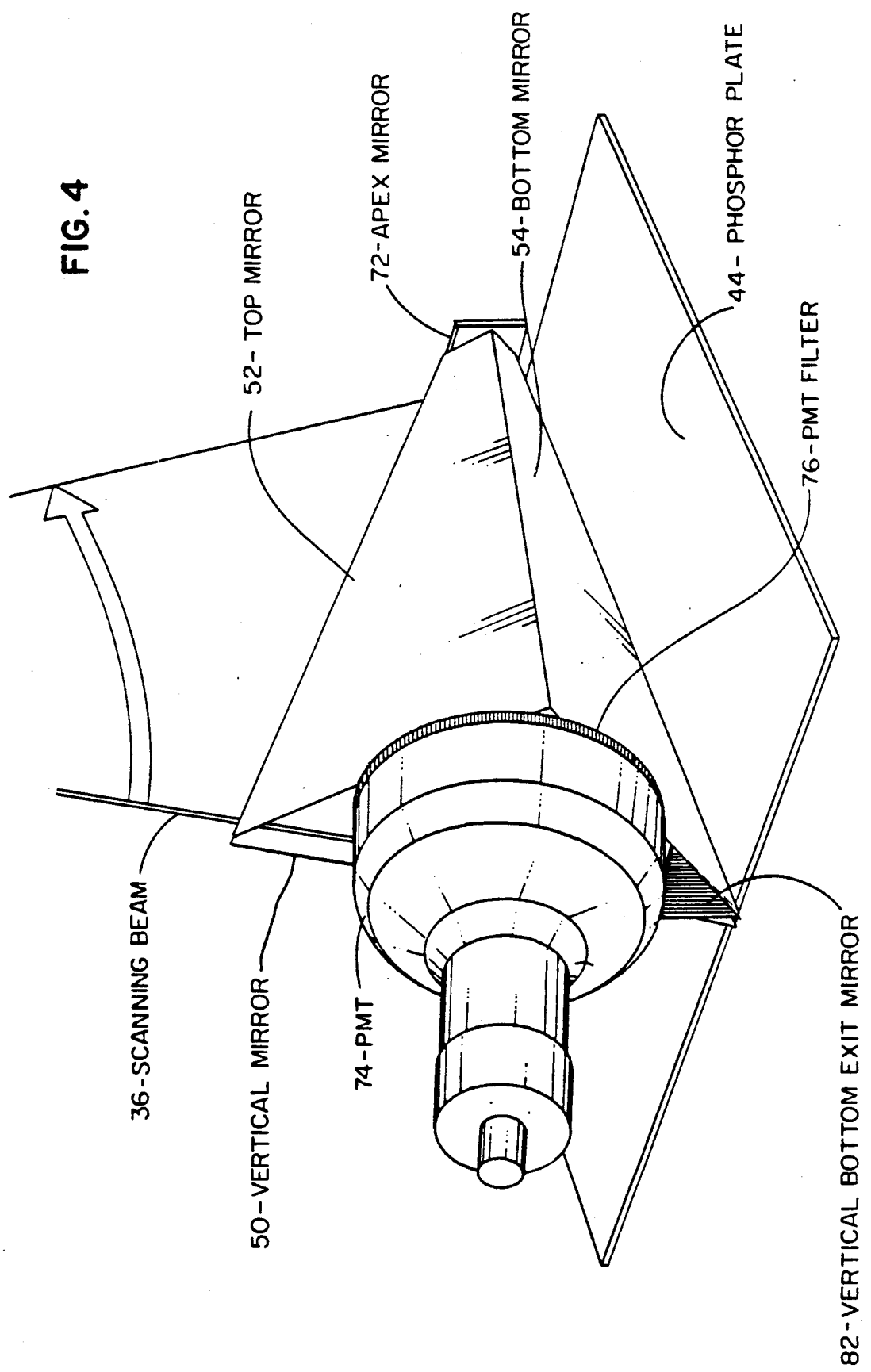

SPLIT V-ROOF MIRROR COLLECTOR HAVING IMPROVED COLLECTION EFFICIENCY

BACKGROUND OF THE INVENTION

1. Technical Field

The invention relates to apparatus for reading out the image stored in a photostimulable phosphor image recording medium. More particularly, this invention relates to apparatus for collecting and detecting the radiation emitted from the photostimulable phosphor in response to interrogation by stimulating radiation.

2. Background Art

In a photostimulable phosphor imaging system, as described in U.S. Pat. No. Re. 31,847, reissued Mar. 12, 1985 to Luckey, a photostimulable phosphor sheet is exposed to an image-wise pattern of short wavelength radiation, such as X-ray radiation, to record a latent image pattern in the photostimulable phosphor sheet. The latent image is read out by stimulating the phosphor with a relatively long wavelength stimulating radiation, such as red or infrared light. Upon stimulation, the photostimulable phosphor releases emitted radiation of an intermediate wavelength, such as blue or violet light, in proportion to the quantity of short wavelength radiation that was received. To produce a signal useful in electronic image processing, the photostimulable phosphor sheet is scanned in a raster pattern by a beam of light produced, for example, by a laser deflected by an oscillating or rotating scanning mirror. The emitted radiation from the stimulated phosphor is sensed by a photodetector, such as a photomultiplier tube, to produce electronic image signals.

In one type of scanning apparatus, the photostimulable phosphor sheet is placed on a translation stage and is translated in a page scan direction past a laser beam that is repeatedly deflected in a line scan direction to form a scanning raster.

To optimize the signal-to-noise ratio of the imaging system, it is desirable to collect as much of the emitted light as possible and to direct it to the photodetector. One form of light collector is proposed in U.S. Pat. No. 4,346,295, issued Aug. 24, 1982 to Tanaka et al. The light collector proposed by Tanaka includes a light guide member comprising a sheet of light transmitting material that is flat on one end and rolled into an annular shape on the opposite end. The flat end of the light collector is positioned adjacent to the scan line on the photostimulable phosphor sheet. The light receiving face of a photomultiplier tube is placed against the annular end of the light guiding member. Such a light collection system has the disadvantages of being expensive and inherently complicated to manufacture. Furthermore, the collection efficiency of transparent light guide members is limited due to their absorption in the wavelength range of light emitted by photostimulable phosphors.

In order to provide an easily manufacturable, low cost, high efficiency light collector, one of the present inventors proposed a double roof mirror light collector in U.S. Pat. No. 4,743,759, issued May 10, 1988, inventor John C. Boutet. As disclosed in this patent, a light collector for collecting and detecting light emitted from a photostimulable phosphor sheet in a photostimulable phosphor imaging system, includes a roof mirror light collector having a bottom roof mirror extending the width of the photostimulable phosphor sheet and a top roof mirror positioned over the bottom roof mirror to define a mirror box having a nearly square cross-section. The roof mirrors define slots along their peaks for passing a scanning beam stimulating radiation through the light box to the surface of the photostimulable phosphor sheet and for admitting emitted light from the photostimulable phosphor sheet into the light box. A photodetector is positioned at an end of the light box to convert collected light into an electronic signal representative of the latent image stored in the phosphor sheet. FIG. 13 of the above-mentioned patent, discloses a light collector which tapers from one end to the other with a light detector at the large end of the collector.

SUMMARY OF THE INVENTION

According to the present invention, there is provided a light collector for collecting and detecting light emitted from a photostimulable phosphor sheet in a photostimulable phosphor imaging system which has high light collection efficiency and ease of manufactureability. According to a feature of the present invention, the light collector includes a vertical mirror and a V-roof mirror facing the vertical mirror having upper and lower mirrors meeting at a right angle apex. The vertical mirror and V-roof mirror form slots for passing a scanning beam of stimulating radiation to a photostimulable phosphor sheet and for admitting emitted light into the mirror collector. The vertical mirror and V-roof mirror form a substantially triangular cross-section having a large dimension located at one end of the photostimulable phosphor sheet and tapering to a small dimension at the other end of the photostimulable phosphor sheet. A photodetector, such as a photomultiplier tube, is positioned at the large open end of the collector to convert collected light into an electronic image signal.

According to further features, the light collection efficiency may be increased by one or more of the following: (1) providing a vertical mirror below the photodetector to reflect emitted light which normally escapes past the photodetector; (2) positioning the photodetector at angles other than 90° with the vertical mirror; (3) placing the photodetector behind the vertical mirror and closing off the large end of the collector with an exit mirror forming an apex with said upper and lower mirrors.

BRIEF DESCRIPTION OF THE DRAWINGS

In the detailed description of the invention presented below, reference is made to the accompanying drawings in which like elements are numbered with like numbers.

FIGS. 4 and 5 are perspective and side elevational views of another embodiment of the present invention;

DESCRIPTION OF THE PREFERRED EMBODIMENT

Figure 1:
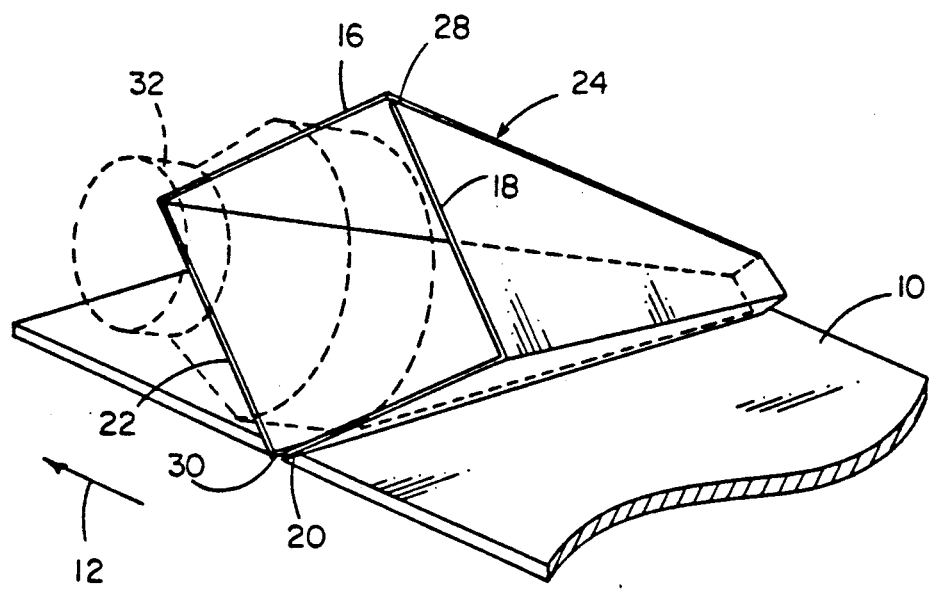
FIG. 1 is a perspective view of a roof mirror light collector useful in describing the background of the present invention.

Referring now to FIG. 1, there is shown an embodiment of a double V-roof mirror collector as described in my U.S. Pat. No. 4,743,759. As shown, a photostimulable storage phosphor plate or sheet 10 is moved in the direction of arrow 12 past a double V-roof mirror light collector 14. Collector 14 include mirrors 16, 18, 20, and 22 which form a box shaped collector which extends across the width of storage phosphor plate 10 and which tapers from a large end 24 to a smaller end 26. Slots 28 and 30 at the top and bottom of the box mirror pass a laser scanning beam of stimulating radiation through the light box collector to the surface of phosphor sheet 10. Light emitted by phosphor sheet 10 is admitted into the light box collector through slot 30 and is reflected by mirrors 16, 18, 20, and 22 into a photomultiplier tube 32.

Although the collector of FIG. 1 has high light collection efficiency and has manufacturing simplicity over prior art light guide member collectors and cylindrical collectors, there are applications where the large size of such collector is inappropriate. The size of the mirrors of the FIG. 1 design can get quite large making for a tall and wide collector envelope at the photomultiplier tube (PMT) end. Moreover, light tends to leak out of the open regions between the photomultiplier tube and the mirror edges. Moreover, the tilt angle of the PMT is constrained by the scan angle of the laser beam.

Figure 2:
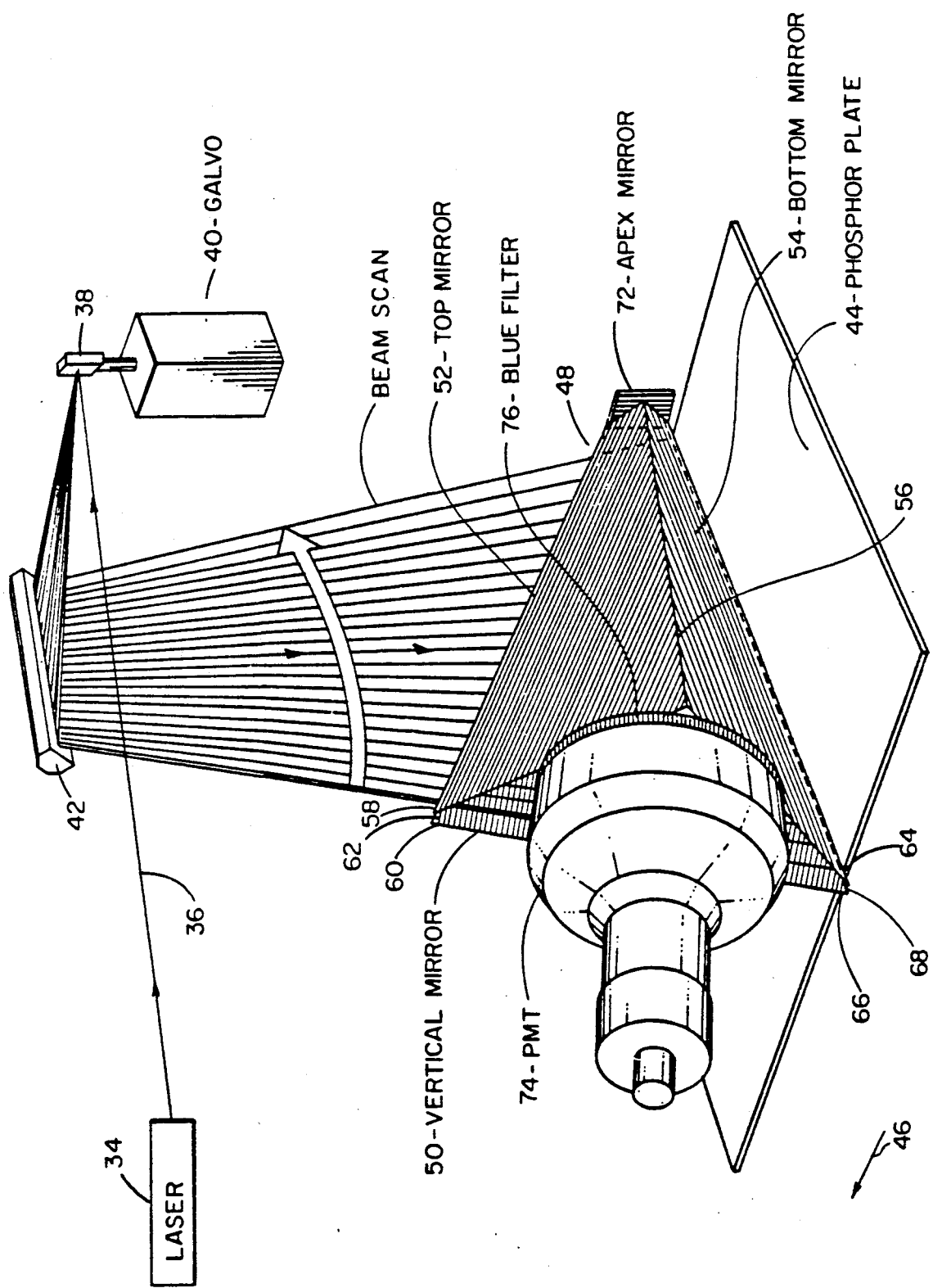
FIG. 2 is a perspective view of an embodiment of the present invention.

Referring now to FIG. 2, there is shown a photostimulable phosphor imaging system having an embodiment of the present invention. Although the embodiment will be described as useful in collecting light in a storage phosphor type system, it will be understood that the collector according to the present invention may be used in other light collecting applications, such as film digitizers or other applications where light is transmitted, reflected or emitted from a surface. As shown in FIG. 2, a laser source 34 emits a laser beam 36 which is reflected from an oscillating mirror 38 driven by galvo 40. A mirror 42 deflects the scanning laser beam 36 to sweep it across a storage phosphor medium such as storage phosphor plate 44 which stores a latent image produced by X-rays. For example, the storage phosphor plate 44 is moved in the direction of arrow 46 so that the plate is scanned in a raster pattern by the coordinated movement of the scanning laser beam 36 across the width of plate 44 and the movement of plate 44 in the direction of arrow 46 under the scanning beam. As used herein, the terms "plate" or "sheet" are not meant to be limiting and the storage phosphor media can take any form other than a plate or sheet, such as a belt, a drum or the like.

The latent image is read out by means of radiation emitted at a wavelength different from the stimulating radiation wavelength of laser beam 36.

According to the present invention, a split V-roof mirror collector 46 is provided to collect the emitted light from storage phosphor plate 44. Collector 46 includes a vertical mirror 50 and upper and lower V-roof mirrors 52 and 54, which form an apex 56, facing vertical mirror 50. The top edge 58 of mirror 52 and the top edge 60 of mirror 50 are spaced apart to form an upper slot 62. A lower edge 64 of mirror 54 and lower edge 66 of mirror 50 are spaced apart and form a bottom slot 68 which is adjacent to storage phosphor plate 44. Slots 62 and 68 are aligned and permit passage of laser scanning beam 36 to stimulate the storage phosphor plate 44. Slot 68 also allows light emitted by storage phosphor plate 44 to be transmitted into collector 48 where it is reflected off mirrors 50, 52, and 54 and an apex mirror 72 into a photodetector comprising photomultiplier tube 74 having a filter 76 which only passes emitted light to PMT 74 and not reflected stimulating light. For example, if the laser beam 36 has a wavelength in the red or infrared region and the light emitted by storage phosphor plate 44 is blue light, filter 76 is a blue filter which passes all emitted radiation to photomultiplier tube 74 but which blocks stimulating radiation of red or infrared light.

Figure 3A:
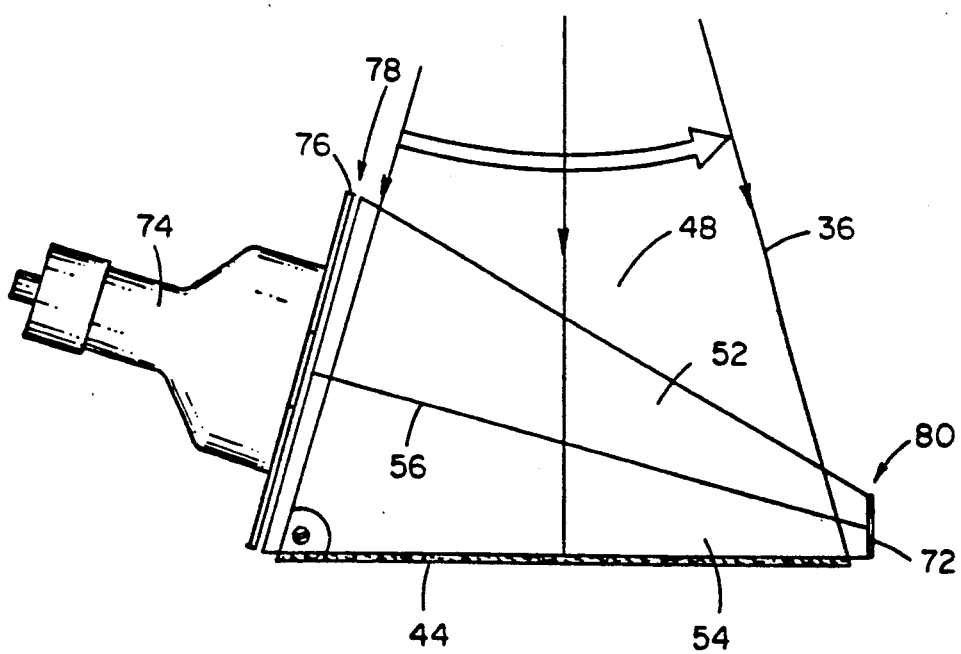
FIGS. 3A and 3B are respective side elevational and top plan views of the embodiment of FIG. 2.
Figure 3B:
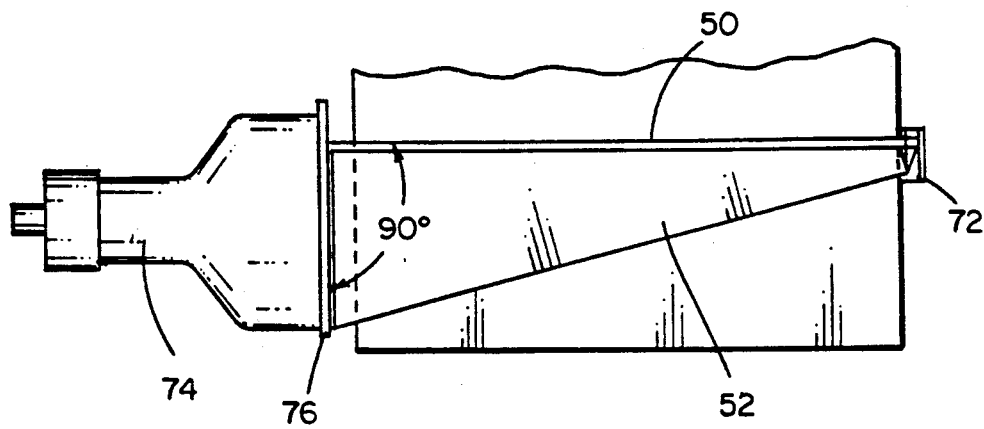

As shown more clearly in FIGS. 3A and 3B, collector 48 spans the width of storage phosphor plate 44 and is tapered from a larger end 78 to a smaller end 80. The larger end 78 is open and locates photomultiplier tube 74. The smaller end 80 of collector 48 is closed off by apex mirror 72.

Mirrors 50, 52 and 54 form a generally triangular cross-section which is tilted at end 78. PMT 74 is also tilted at the same angle which is determined by the angle of incidence $\theta$ of the laser beam relative to storage phosphor plate 44. The face of PMT 74 forms a 90° angle with vertical mirror 50. Mirrors 50, 52, 54, and 70 are highly specularly reflective and preferably have peak specular reflection efficiency at the wavelength of the radiation emitted by storage phosphor plate 44.

Figure 5:
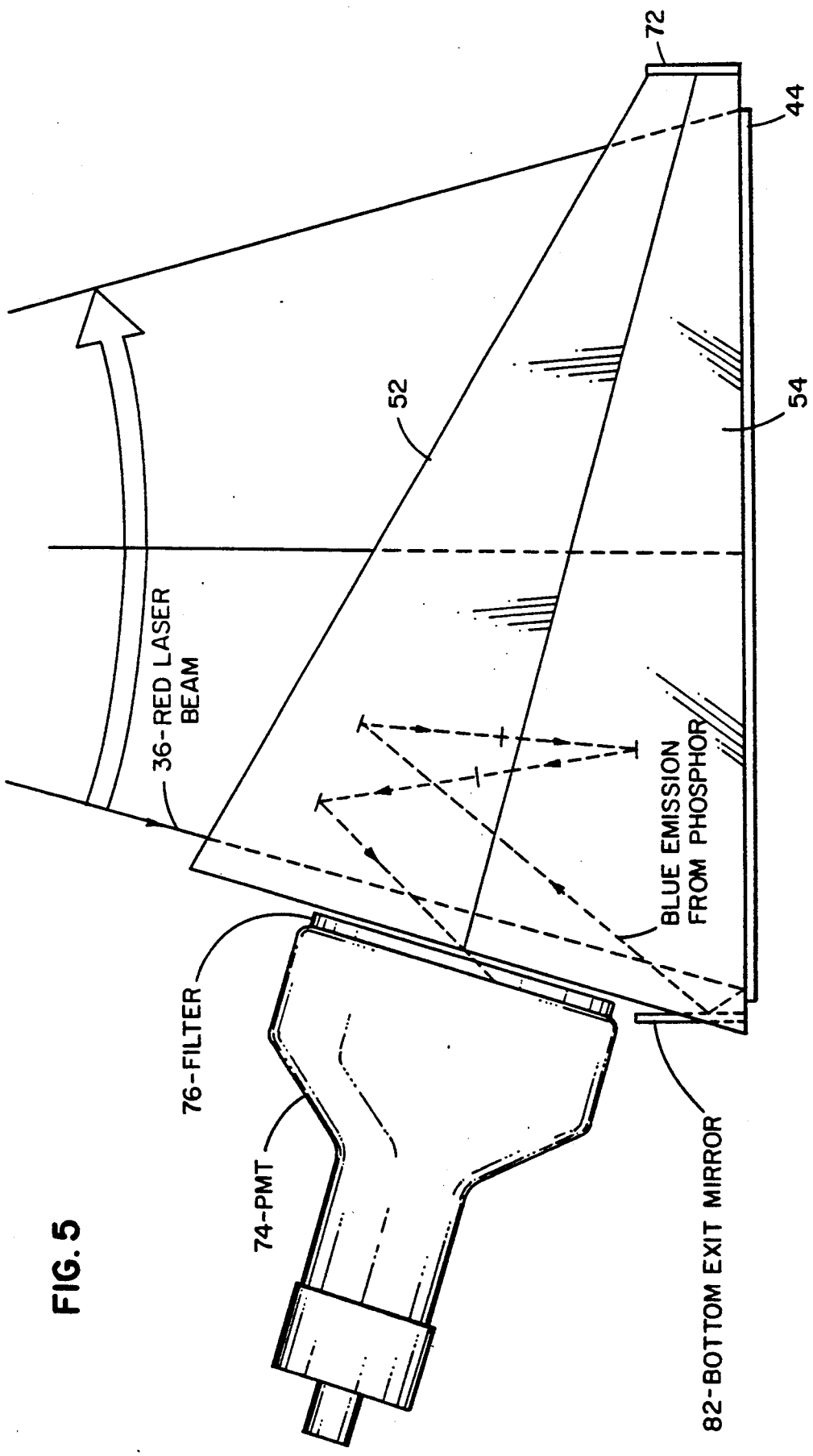

With reference to FIGS. 4 and 5, there is shown an embodiment of the present invention in which light collection efficiency near PMT 74 is improved. As shown, a vertical exit mirror 82 is positioned below PMT 74 and reflects emitted light, which normally escapes past PMT 74, back into collector 48. Part of this emitted light eventually reaches PMT 74 where it is detected. By orienting mirror 82 vertically rather than at the tilt angle of PMT 74, reflection of stimulating light back to plate 44 is inhibited thus minimizing flare near PMT 74.

Figure 6A:
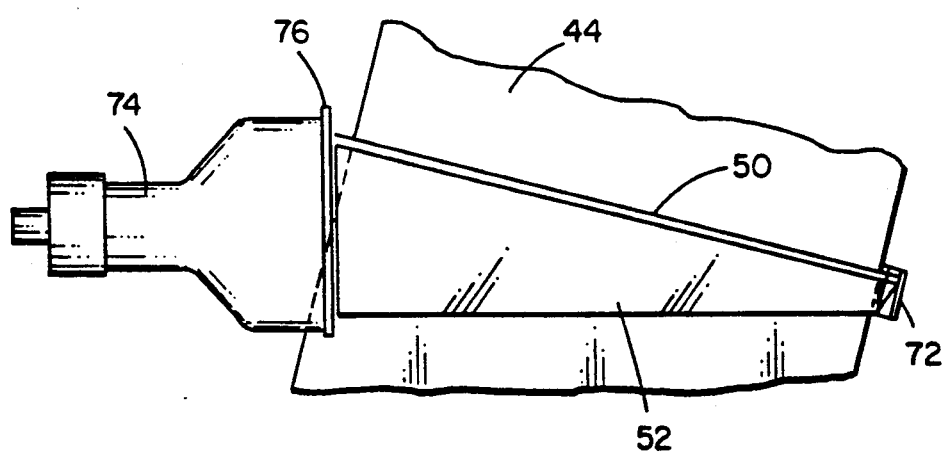
FIGS. 6A and 6B are respective top plan views showing other embodiments of the present invention.
Figure 6B:
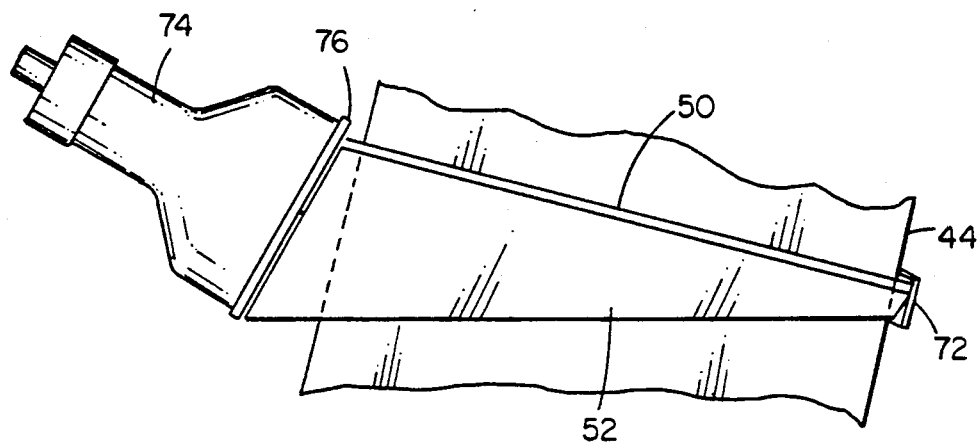

As shown in FIGS. 6A and 6B, PMT 74 and exit mirror 82 are angled at other than 90° to the plane of vertical mirror 50. When the angle is greater than 90°, stimulating light cannot be reflected directly by exit mirror 82 to phosphor plate 44. Thus, flare is minimized while collection efficiency is improved.

Figure 7A:
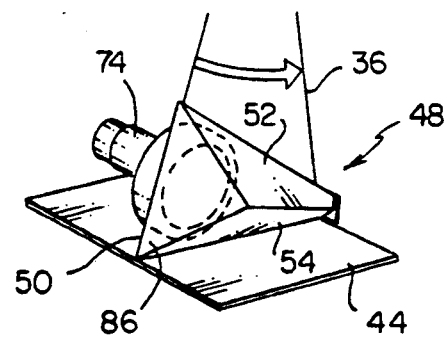
FIGS. 7A, 7B and 7C are respective perspective, top plan and side elevational view of another embodiment of the present invention.
Figure 7B:
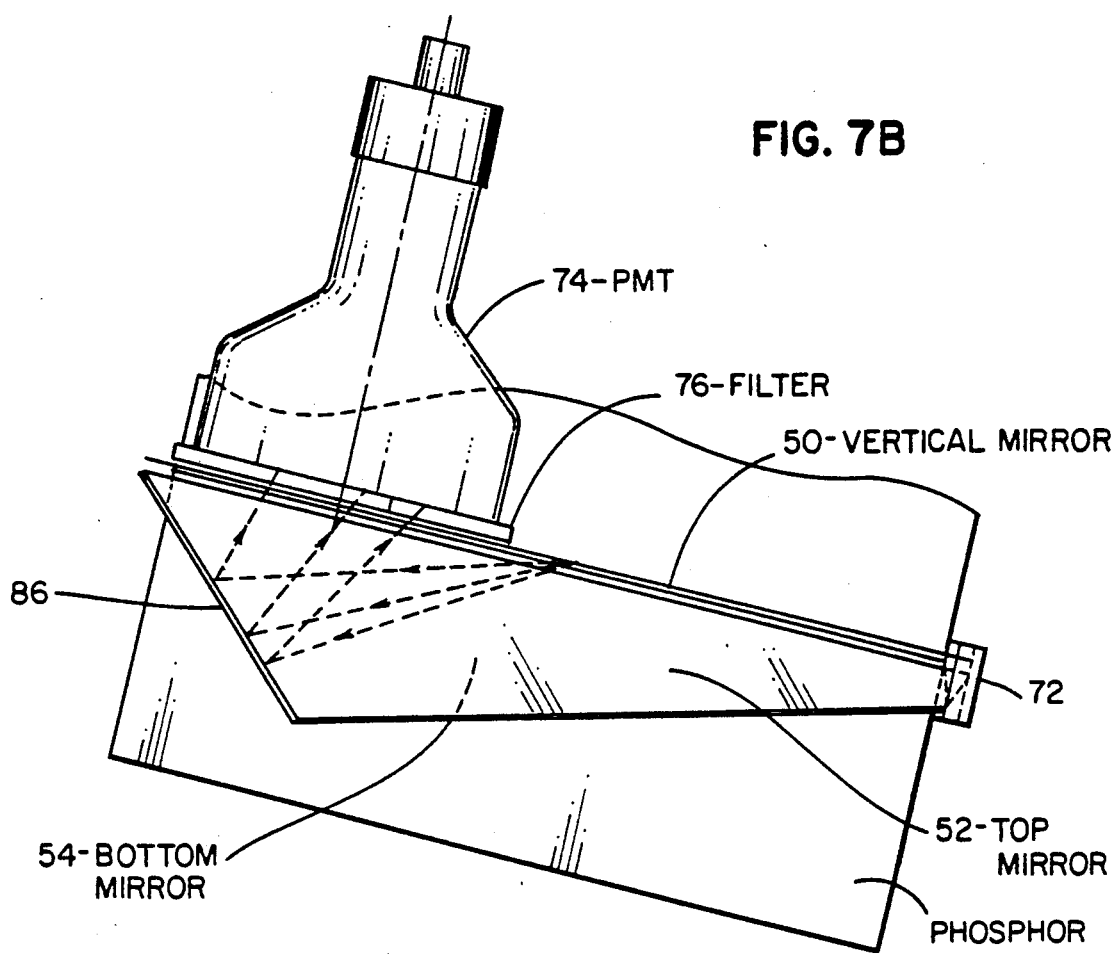
Figure 7C:
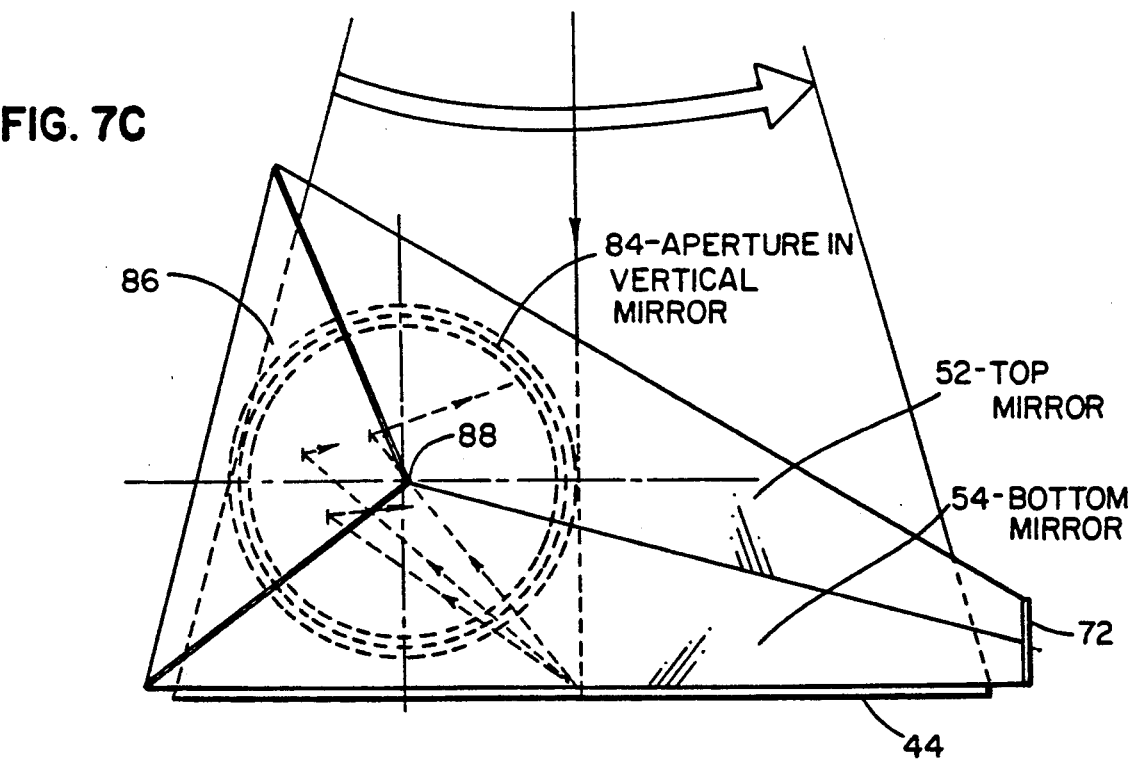

In the embodiment of the invention shown in FIGS. 7A, 7B and 7C, PMT 74 is placed behind the plane of vertical mirror 50. Emitted light reaches PMT 74 through aperture 84 in mirror 50. An exit deflector mirror 86 closes off the large end of collector 48 and forms a pyramidal structure with mirrors 52 and 54 having an apex 88 substantially centered on the face of PMT 74. Because of the location of PMT 74, collector 48 need not be much wider than phosphor plate 44, thus providing a compact design. In order to reduce flare, mirror 86 can be made to absorb stimulating light while reflecting emitted light.

INDUSTRIAL APPLICABILITY AND ADVANTAGES

The split V-roof mirror light collector of the present invention, is useful in a photostimulable phosphor scanning apparatus. It has the advantages of high light collection efficiency, ease of manufacture, compact design, and noninterference with the laser scanning beam.

Although the invention has been described with reference to preferred embodiments thereof, it will be understood that variations and modifications can be effected within the spirit and scope of the invention as described above and as defined in the appended claims.

What is claimed is:

1. A light collector for collecting and detecting light emitted, reflected or transmitted from a scanned information medium comprising:

a vertical mirror extending the width of the scanned medium and having a lower edge adjacent to the scanned medium and an upper edge;

a V-roof mirror located adjacent to said vertical mirror and having upper and lower mirrors forming an apex facing said vertical mirror, said upper mirror having an edge adjacent to and spaced from said upper edge of said vertical mirror and said lower mirror having an edge adjacent to and spaced from the lower edge of said vertical mirror thereby to form aligned slots for the passage of a scanning beam of radiation to a medium to be scanned and for allowing light emitted, reflected or transmitted by the scanned medium to enter the collector;

wherein said vertical mirror and said upper and lower mirrors of said V-roof mirror form a substantially triangular cross-section which tapers from a large end of said collector to a small end of said collector;

photodetector means having a light receiving face located at the large end of said light collector for receiving light reflected by said collector and for generating an electrical signal in response thereto; and a vertical exit mirror located below said photodetector means.

2. The light collector of claim 1 wherein said photodetector means and said vertical mirror form an angle with said vertical mirror other than 90°.

3. A light collector for collecting and detecting light emitted, reflected or transmitted from a scanned information medium comprising:

a vertical mirror extending the width of the scanned medium, having a lower edge adjacent to the scanned medium and an upper edge, having an aperture;

a pyramidal mirror located adjacent to said vertical mirror and having upper, lower and exit mirrors forming an apex facing said vertical mirror, said upper mirror having an edge adjacent to and spaced from said upper edge of said vertical mirror and said lower mirror having an edge adjacent to and spaced from the lower edge of said vertical mirror thereby to form aligned slots for the passage of a scanning beam of radiation to a medium to be scanned and for allowing light emitted, reflected or transmitted by the scanned medium to enter the collector;

wherein said vertical mirror and said upper and lower mirrors of said pyramidal mirror form a substantially triangular cross-section which tapers from a large end of said collector which is closed off by said exit mirror to a small end of said collector; and photodetector means having a light receiving face located at said aperture in said vertical mirror for receiving light reflected by said collector and for generating an electrical signal in response thereto.

4. A mirror light collector for collecting and detecting light emitted from a photostimulable phosphor medium scanned by a beam of stimulating radiation comprising:

a vertical mirror extending the width of the photostimulable phosphor medium, said vertical mirror having an upper edge and a lower edge located adjacent to said stimulable phosphor medium;

a split V-roof mirror having upper and lower mirrors facing said vertical mirror, said upper mirror having an edge adjacent to and spaced from said upper edge of said vertical mirror and forming an upper slot and said lower mirror having a lower edge adjacent to and spaced from said lower edge of said vertical mirror and forming a slot aligned with said upper slot, wherein said upper and lower slots pass a beam of stimulating radiation to said photostimulable phosphor medium and said lower slot allows light emitted by said phosphor medium to enter said light collector;

wherein said vertical mirror and upper and lower mirrors of said V-roof mirror form a generally triangular cross-section which tapers from a large end of said collector to a small end of said collector;

photodetector means having a light receiving face located at the large end of said light collector for receiving light emitted by said photostimulable phosphor medium and for generating an electrical signal in response thereto; and a vertical exit mirror located below said photodetector means.

5. The light collector of claim 4 wherein said photodetector means and said vertical mirror form an angle with said vertical mirror other than 90°.

6. A mirror light collector for collecting and detecting light emitted from a photostimulable phosphor medium scanned by a beam of stimulating radiation comprising:

a vertical mirror extending the width of the photostimulable phosphor medium, said vertical mirror having an upper edge, a lower edge located adjacent to said stimulable phosphor medium, and having an aperture;

a pyramidal mirror having upper, lower and exit mirrors which form an apex facing said vertical mirror, said upper mirror having an edge adjacent to and spaced from said upper edge of said vertical mirror and forming an upper slot and said lower mirror having a lower edge adjacent to and spaced from said lower edge of said vertical mirror and forming a slot aligned with said upper slot, wherein said upper and lower slots pass a beam of stimulating radiation to said photostimulable phosphor medium and said lower slot allows light emitted by said phosphor medium to enter said light collector;

wherein said vertical mirror and upper and lower mirrors of said pyramidal mirror form a generally triangular cross-section which tapers from a large end of said collector which is closed off by said exit mirror to a small end of said collector; and photodetector means having a light receiving face located at said aperture in said vertical mirror for receiving light emitted by said photostimulable phosphor medium and for generating an electrical signal in response thereto.

* * * * *